United States Patent [19]  
Furuta et al.

[11] 4,409,106  
[45] Oct. 11, 1983

[54] APPARATUS AND METHOD FOR SEPARATING BLOOD COMPONENTS

[75] Inventors: Tadaaki Furuta; Shuusaku Tabata, both of Fuji, Japan

[73] Assignee: Asahi Kasei Kogyo Kabushiki Kaisha, Osaka, Japan

[21] Appl. No.: 369,439

[22] Filed: Apr. 19, 1982

[30] Foreign Application Priority Data

Sep. 8, 1981 [JP] Japan .................... 56-141216  
Sep. 8, 1981 [JP] Japan .................... 56-141217  
Nov. 26, 1981 [JP] Japan .................... 56-188320

[51] Int. Cl.³ .............................................. B01D 21/01  
[52] U.S. Cl. .................................... 210/732; 210/800; 210/802; 210/198.1; 210/521; 210/927; 436/177  
[58] Field of Search ................. 210/732–736, 210/800–804, 198.1, 199, 207, 208, 521, 522, 927; 422/44; 436/177

[56] References Cited  
U.S. PATENT DOCUMENTS

| 1,946,414 | 2/1934 | Schmid | 210/802 |
| 2,375,590 | 5/1945 | Schonberg | 210/521 |
| 3,677,710 | 7/1972 | Hirsch | 210/927 |
| 3,933,654 | 1/1976 | Middelbeek | 210/521 |
| 4,028,249 | 6/1977 | McGivern | 210/521 |
| 4,255,256 | 3/1981 | Ferrante | 210/927 |
| 4,353,246 | 10/1982 | Farber | 210/927 |

Primary Examiner—Ernest G. Therkorn  
Attorney, Agent, or Firm—Sprung, Horn, Kramer & Woods

[57] ABSTRACT

An apparatus and method for effectively and efficiently separating blood components by means of sedimentation action due to gravitational force are disclosed. The blood to be separated is continuously passed through a blood flow channel comprising plural flat empty spaces each having a thickness of, for example, 20 mm or less, or a plurality of tubular empty spaces each having a sectional area of, for example, 3 cm or less. An opening for a feed line is provided in a first empty space of the apparatus and two or more openings for discharge lines of the separated blood components are provided in a second empty space. These empty spaces are connected with the blood flow channel.

12 Claims, 7 Drawing Figures

APPARATUS AND METHOD FOR SEPARATING BLOOD COMPONENTS

BACKGROUND OF THE INVENTION

1. Field of the Invention

The present invention relates to an improved apparatus and method for separating blood components from blood by means of sedimentation action due to gravitational force.

2. Description of the Prior Art

Blood comprises a plasma component and a blood corpuscle component containing erythrocytes, leucocytes, blood platelets and the like. Recently, remarkable developments in so-called artificial organs have led to the practical use of therapeutic treatment in which blood is removed from the human body by extracoporeal circulation and subjected to a dialysis treatment or an adsorption treatment after fractionation. Such therapeutic treatment has become more and more important. It is strongly required, however, that it does not adversely affect the body. For this reason, the apparatus for the therapeutic treatment must satisfy various factors. One of these factors is that the apparatus should not remove the protein components contained in the patient's blood. For example, an artificial kidney should not discharge plasma protein along with the waste liquid.

Recently, it has been learned that an abnormal increase of high molecular weight solutes such as immune complexes, cryopricipitates, aggregates of immunoglobulin and nucleic acids in blood strongly influences the occurence and condition of autoimmune diseases. Therefore, plasma exchange therapy is carried out to remove said high molecular weight solutes.

Furthermore, in the field of blood transfusion, hospitals have not been transfusing collected blood whole, but have been frequently separating the collected blood into its components so as to use the specific blood component required by the patient. One method of doing this is to allow the blood to stand, wherein the blood corpuscle component gradually settles to the bottom and separates from the plasma. However, this gravitational method of separation is very slow. For this reason, hospitals have heretofore widely used centrifugal separation for separating blood components rather than gravitational separation. Centrifugal separation, however, is disadvantageous in that it requires an expensive centrifugal separator, which in turn requires high rotational power and safety devices.

Accordingly, the objects of the present invention are to eliminate the above-mentioned disadvantages of the prior arts and to provide an apparatus and method for effectively and efficiently separating blood components, without using centrifugal force, by means of sedimentation action due to gravitational force.

Other objects and advantages of the present invention will be apparent from the description set forth hereinbelow.

In accordance with the present invention, there is provided an apparatus for separating blood components by means of sedimentation action due to gravitational force, comprising:

a first empty space provided with an opening for a feed line of blood;

a component separation portion in connection with said empty space, the inside of the separation portion forming a plurality of flat or tubular blood flow channels; and a second empty space provided with at least two openings for discharge lines of the separated blood components.

In accordance with the present invention, there is also provided a method for separating blood components by means of sedimentation action due to gravitational force, comprising the steps of:

continuously passing blood to be separated through blood flow channels comprising at least two flat or tubular empty spaces, said blood containing an added water-soluble polymer, while the blood flow channels are filled up;

separating the blood flow into multiple streams of the separated blood component layers; and collecting the desired blood component layer or layers.

The present invention will be better understood from the description set forth below with reference to the accompanying drawings, in which.

Figure 1:
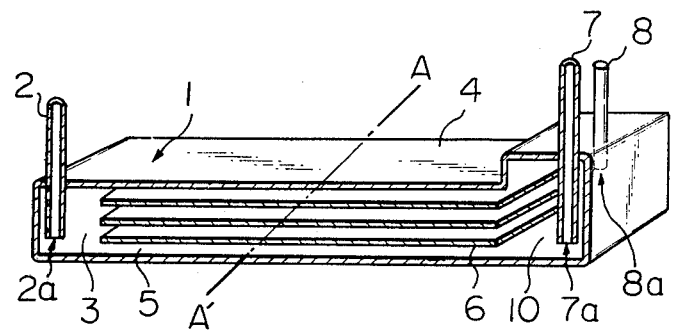
FIG. 1 is a perspective view illustrating one embodiment of the blood component separation apparatus of the present invention having flat blood flow channels, in which the front is cut so that the inside thereof is clearly understood.
Figure 2:
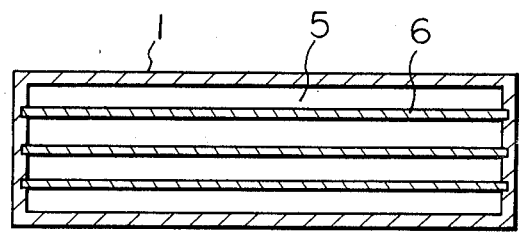
FIG. 2 is a front cross-sectional view of the apparatus shown in FIG. 1, taken along the line A—A' in FIG. 1, in which one embodiment of the flat type blood flow channel is shown.
Figure 3:
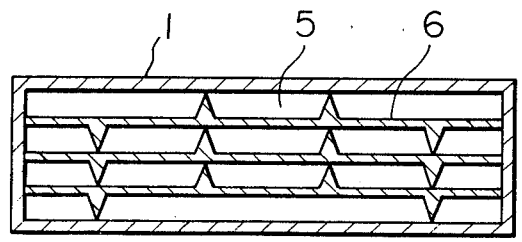
FIG. 3 is a cross-sectional view illustrating another embodiment of the flat type blood flow channel.

Surprisingly, the present inventors have found that cohesive masses of erythrocytes in the form of linked coins, caused by the adhesion between the erythrocytes after passing the blood through a narrow space, do no tend to dissociate, thereby facilitating the sedimentation. Thus, blood can be efficiently and continuously separated into its components, without applying centrifugal force.

The reason why the desired blood component or components can be efficiently separated from the blood according to the present invention is not clearly understood, but it would seem as follows. Although blood is a viscous liquid, the factor substantially deciding the viscosity is the ratio of volume of erythrocytes to the whole blood, i.e. a hematocrit value. The hematocrit value of normal human blood is 30 through 45% and the viscosity of the normal human blood is 3 through 4 times that of water. When the hematocrit value reaches 60 through 70%, the viscosity of the blood becomes as high as 6 through 9 times that of water. On the other hand, the viscosity of the plasma component in the blood is only 1.5 through 2.0 times that of water, although it depends upon the amount and types of proteins contained in the blood. According to the observation, if blood is once slightly separated into a supernatant layer and a sedimentation layer, when flowing, by erythrocyte sedimentation and other factors, the viscosity of the sedimentation layer is increased. The higher viscosity of the sedimentation layer then creates greater resistance in the sedimentation layer against the external force causing the blood flow. Contrary to this, the lower viscosity of supernatant layer means less resistance against said external force. On the other hand, the viscosity of blood is largely affected by the linear velocity of the blood flow. That is, the lower linear velocity rapidly increases the viscosity of the blood. It appears that this phenomenon is caused by the function of cohesion, especially the adhesion between erythrocyte particles. Actual microscopic observation showed that the erythrocytes tended to form cohesive masses. These cohesive masses are frequently in the form of linked coins. This phenomenon seems to be another factor increasing the resistance of the flow. Furthermore, it is believed that the filled state of the blood flow channel during the blood flow facilitates the formation of the cohesive masses of the erythrocytes and their concentration, because, in addition to the compressing effect of the erythroctye sedimentation (i.e. compressing effect due to downward gravitational force), the sedimentation layer is compressed by the flow (i.e. compressing effect due to lateral external force). Still furthermore, the cohesive masses of the erythrocytes in the form of linked coins, caused by the adhesion between erythrocytes, are not readily dissociated, for example, in the course of gentle mixing caused by, for example, the change of the sizes of the blood flow channels, and, therefore, are rapidly sedimented. It is believed that these phenomena of the blood under a flowing condition effect the blood component separation of the present invention. That is to say, according to the present invention, blood components can be efficiently separated without any moving parts and by just passing blood through blood flow channels composed of a narrow space.

The present invention can separate whole blood or a liquid containing, as a main constituent, whole blood and, as a minor constituent, a special blood component, anticoagulant or the like.

The component separation portion according to the present invention can be composed of a plurality of flat blood flow channels or a plurality of tubular blood flow channels. Of these flow channels, the use of the flat flow channel, for example, a long rectangular form, having a large area is desirable, since a large amount of blood can be treated.

Blood flow channels comprising a thin flat empty space can be desirably used in the present invention, since the downward force due to erythrocyte sedimentation (i.e. gravitational force) and lateral external force due to the flow of the blood are effectively forced to the erythrocytes and the formation of the cohesive masses is facilitated. The thickness of the flat blood flow channel is 20 mm or less, preferably, 0.2 through 10 mm, and more preferably 0.5 through 5 mm.

Blood flow channels in the form of a tube having a small sectional area is desirably used in the present invention, since the interaction between the erythrocytes is strengthened. The sectional area of the tubular flow channel is 3 $cm^2$ or less, preferably 0.0003 through 1 $cm^2$ and more preferably 0.001 through 0.5 $cm^2$.

In the case where the thickness of the flat flow channel is less than 0.2 mm or the sectional area of the tubular flow channel is less than 0.0003 $cm^2$, the efficiency of the separation of the plasma and the blood corpuscles tends to decrease under practical linear velocity conditions. It is believed that the above-mentioned reduction in separation efficiency is caused by a phenomenon similar to the so-called Fahraeus-Lindqvist effect. (That is, when blood flows in capillaries, blood corpuscles do not randomly flow, but are forced to flow in an oriented condition, whereby the viscosity is abnormally decreased.)

The ratio of the length L ($cm^2$) of the flow channel to the inlet sectional area S ($cm^2$) of the flow channel (i.e. L/S) in the blood flow channel of the present invention is desirably 10 or more to strengthen the interaction of the erythrocytes.

The tubular blood flow channels can be in the form of any shape, for example, a circular column, an elliptical column or a hexagonal column. Tubes in the form of circular columns and hexagonal columns can be suitably used in the present invention because they can be readily bundled together and adhered to one another. By the use of these tubular materials, the apparatus for separating blood components can be readily manufactured.

The separation portion having a plurality of flat blood flow channels can be readily made by heaping up multiple flat plates at a constant distance. For instance, spacers can be inserted between the flat plates, to ensure a fairly constant thickness of the blood flow channel. Plates with protrusions having an appropriate height can also be laminated to further divide the spaces into smaller sections.

The linear velocity of the blood flow is desirably 0.5 through 200 mm/min, more desirably 1 through 100 mm/min, and most desirably 2 through 50 mm/min. In the case where the linear velocity of the blood flow is larger than 200 mm/min, effective and efficient blood component separation becomes difficult, as it is likely to cause a turbulent flow and remarkably weaken the cohesion between the erythrocyte particles. On the other hand, in the case where the linear velocity of the blood flow is smaller than 0.5 mm/min, the capacity for treatment of the blood is reduced. Although the length of the blood flow channel can be shortened, in such case, in order to increase the capacity for treatment of the blood, the width of the blood flow channel would hava to be increased. Such an increase, however, would likely cause channelling of the blood. The width of the blood flow channel is desirably 50 through 500 mm, more desirably 100 through 300 mm.

In the apparatus according to the present invention, the second empty space having the openings for the discharge lines of the separated blood components desirably has approximately the same or less volume than the total volume of a plurality of the blood flow channels in the component separation portion. On the other hand, since the first empty space having an opening for the feed line of the blood is provided for distributing the blood to be fed into a plurality of the blood flow channels as uniform as possible, it may be any shape so long as said purpose is attained. However, the volume of the first empty space is desirably as small as possible.

From a practical point of view, the volume of the apparatus according to the present invention is at least 50 ml. Furthermore, when the apparatus of the present invention is used for the purpose of extracoporeal circulation of human blood by connecting the apparatus to a human blood vessel, or when separating a one-man portion of collected blood contained in a blood bag the volume of the apparatus is desirably 500 ml or less.

The flow rate of the blood is such that the residence time of the blood in the blood flow channel is desirably 2 through 20 min, more desirably 4 through 15 min, although it may be varied depending upon, for example, the shape or the volume of the blood flow channel. A too short residence time causes insufficient blood separation due to a too large flow rate of the blood. On the other hand, the two long residence time results in the undesirably small volume of the separated blood component or components obtained by the apparatus due to the too small flow rate of the blood. As a general trend, the narrower the thickness of the blood flow channel or the smaller the sectional area of the blood flow channel, the greater the amount of the separated blood component or components obtainable in a short residence time.

The term "residence time T (min)" used herein is defined by the following equation:

$$T = V/Q$$

Wherein
V: total volume of blood flow channels (ml)
Q: flow rate of blood (ml)

The temperature of the blood flow is desirably 35° through 42° C., more desirably 37° through 40° C. The separation efficiency becomes large, as the temperature of the blood to be separated becomes high. However, in the case where the temperature of the blood becomes too high, the hemolysis of the erythrocytes and the denaturation of enzymes might be caused.

The apparatus according to the present invention should be made of rigid materials which will not deform by inside pressure. Furthermore, the apparatus should be nontoxic and antithrombosis materials. The materials which can be used in the manufacture of the apparatus include, for example, synthetic resins such as polycarbonate resin, polypropylene resin, polyethylene resin, polyvinyl chloride resin and acrylic resin and metals such as aluminum and stainless steel. The apparatus of the present invention can also be made of a nonrigid material such as silicone resin and the periphery of the apparatus can be supported in a stiff material such as a shell made of, for example, aluminum. In the case of the metallic shell, an appropriate heater can be embedded therewithin to facilitate the heating of the blood.

The blood flow channels are desirably mounted in such a manner that the blood to be separated flows in the blood flow channel in an upward direction at an angle more than the substantial horizontal plane but less than approximately 45°. The term "substantial horizontal plane" includes an inclination within approximately ±10° from the horizontal plane. The blood flow channels are desirably composed of smooth surfaces. However, relatively rough surfaces can also be used.

Surprisingly, the present inventors have further found that the previous addition of a water-soluble polymer to the blood to be separated in a small blood separating apparatus promotes the very effective cohesion of the erythrocytes and, therefore, the supernatant layer can be rapidly collected.

The water-soluble polymers usable for this purpose include, for example, gelatin and the derivatives thereof, polysaccharides such as dextran, inulin and the derivatives thereof and water-soluble polyvinyl compounds such as polyvinyl alcohol, poly-vinyl pyrrolidone and the derivatives thereof. The water-soluble polymers having a molucular weight of more than 1000 accelerate the cohesion of the erythrocytes. However, the use of water-soluble polymers having a too large molecular weight is not recommendable due to the facts that they have antigenic properties and also that they adversely affect the kidney. Accordingly, water-soluble polymers having a molecular weight of less than 100,000 but more than 1000, more preferably less than 50,000 but more than 1000 can be suitably used in the present invention.

The water-soluble polymers are desirably used in the form of an aqueous solution having the approximately same osmotic pressure as the physiological osmotic pressure, in order to continuously separate the blood components according to the present invention. The desired concentration range of the water-soluble polymers in water is within the range of from 1 to 10% by weight. The amount of the aqueous water-soluble polymer solution added to the blood is desirably within the range of from 10 to 25% by volume.

The preferred embodiments of the present invention will now be illustrated in detail in connection with the accompanying drawings.

In FIG. 1, a sealed vessel 1 comprises an empty space (A) 3 having an opening 2a for a blood feed line 2, flat blood flow channels 5 contained in a component separation portion 4 and connected with the empty space (A), and an empty space (B) 10 connected with the component separation portion 4. The blood, usually containing an anticoagulant, is continuously fed through a feed line via an opening 2a to the empty space (A) 3 and each blood flow channel 5. The blood thus fed is gradually separated, by the blood cohesion, along the blood flow channel into a supernatant layer comprising platelet rich plasma and a sedimentation layer comprising blood corpuscles containing erythrocytes and leucocytes. The sedimentation layer is sometimes further separated, whereby a leucocyte layer floating on an erythrocyte layer is formed, as an intermediate layer. The separated components are continuously discharged from an empty space (B) 5 via openings 7a and 8a, which are located in each component layer, through a discharge line 7 and a discharge line 8. In this case, the openings 7a and 8a are provided at the lowermost portion and the uppermost portion of the blood component streams at the end of the downstream side of the empty space (B), respectively. Thus, the blood corpuscles are discharged through the discharge line 7 and the platelet rich plasma is discharged through the discharge line 8.

In order to prevent the contamination of the supernatant layer by the components of the sedimentation layer, the discharge rate of each separated component can be advantageously controlled by means of a detection means such as an optical type detector, whereby the separation boundary surface between the supernatant layer and the sedimentation layer can be controlled to a predetermined desired level. As a detector, an optical type detector can be suitably used due to the fact that an optical type detector does not adversely affect the separated components. Generally speaking, an optical type detector is suitable for use in the detection of the contamination of plasma by blood corpuscles rather than detection of the contamination of blood corpuscles by plasma.

For better effect, one can previously add plasma to the blood to be introduced through the feed line 2. This previous addition of plasma to the blood increases the amount of the platelet rich plasma discharged through the discharge line 8. Experiments have confirmed, however, that even when said previously added plasma contains substantially no platelets, the amount of platelets contained per unit amount of the platelet rich plasma discharged through the discharge line 8 decreases at a smaller rate than said increase in the amount of platelet rich plasma. As a result, the amount of the separated and discharged blood platelets per unit time is increased.

Furthermore, as mentioned hereinabove, the erythrocyte sedimentation effect is essential to the present invention. However, the erythrocyte sedimentation effect is sometimes small for certain types of blood to be separated, especially when the blood is in the state of polycythemia. In this case, the inclusion of plasma in the blood to be fed increases the effect of the present invention.

In addition, in the case of very anemic blood having a hematocrit value of 20% or less, concentrated erythrocytes can be previously added to the blood to be fed, or a portion of the blood corpuscles discharged from the discharge line 9 can be previously added to the blood to be fed, to effectively increase the probability of erythrocyte cohesion.

Figure 4:
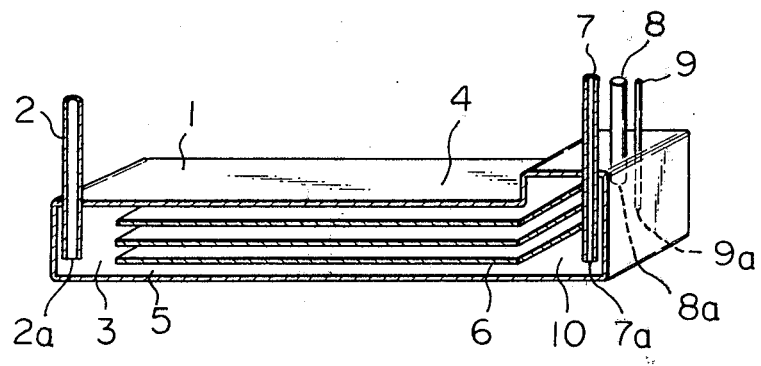
FIG. 4 is a schematic view illustrating one embodiment of the blood component separation apparatus having a plurality of the flat type blood flow channels.

In FIG. 4, a vessel 1 contains another opening 9a connected with a discharge line 9 and located at an intermediate level between the opening 7a connected with the discharge line 7 and the opening 8a connected with the discharge line 8. In the case where the separation boundary surface of the supernatant layer and the sedimentation layer moves up from the level of the opening 9a, the component of the sedimentation layer can be discharged through the opening 9a. On the other hand, when said boundary surface moves down from the level of the opening 9a, the component of the supernatant layer can be discharged through the opening 9a. Thus, the level of said separation boundary surface can be controlled to a desired level and the contamination of the platelet rich plasma discharge through the discharge line 8 by the component of the sedimentation layer can be eliminated. When the separation further proceeds, an intermediate layer of leucocytes sometimes forms and floats on the erythrocyte layer. This intermediate layer of leucocytes can also be discharged through the opening 9a to the outside of the system.

Figure 5:
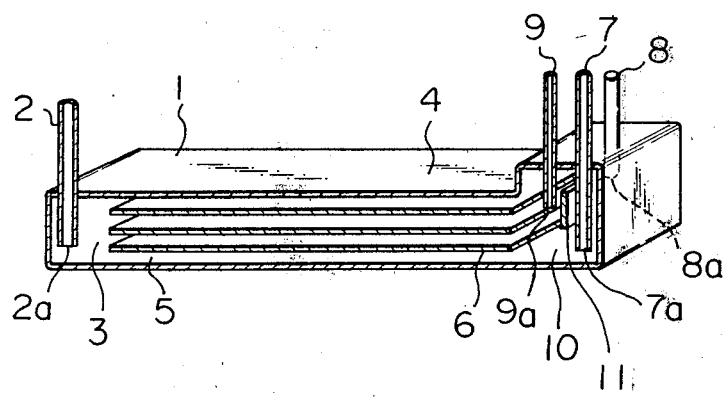
FIG. 5 is a schematic view illustrating a further embodiment of the blood component separation apparatus according to the present invention, in which a plurality of the flat type blood flow channels are contained.

In FIG. 5, a weir 11 is mounted at the downstream side of the blood flow channel 4 of the vessel 1 but at the upstream side of the empty space (B) 10 in such a manner that only the flow of the intermediate layer containing a large amount of leucocytes can be blocked. In order to discharge the blocked intermediate layer, an opening 9a is provided at the upstream side of the weir 11. Thus, an intermediate layer comprising a large amount of leucocytes can be obtained as leucocyte rich blood, together with a supernatant layer comprising platelet rich plasma and a sedimentation layer comprising erythrocytes. The component of the sedimentation layer is often included in the intermediate layer obtained. Accordingly, the intermediate layer discharged through the discharge line 9 is introduced into another apparatus of the present invention, wherein the component of the sedimentation layer can be sedimented and removed.

The experimental method of separating blood components of fresh blood will be explained with reference to FIG. 7 in which a schematic view illustrating one embodiment of the blood component separation system for an experimental practice of the present invention.

The blood component separation apparatus 11 of the present invention and a fresh blood storage vessel 16 containing fresh blood are warmed in a constant temperature bath 12. The blood contained in the vessel 16 is fed to the apparatus 11 by means of a pump 13. The platelet rich plasma separated in the apparatus 11 is pumped up by a pump 14 and collected in a platelet rich plasma receiving vessel 18. When an erythrocyte concentration of the platelet rich plasma, the pump 14 is stopped. The erythrocyte concentrated blood is discharged from the apparatus 11 and collected in an erythrocyte concentrated blood receiving vessel 17.

As mentioned hereinabove, according to the present invention, blood components can be separated by using a very simple and compact means, without applying centrifugal force to the blood, whereby erythrocyte concentrated blood and platelet rich plasma, erythrocyte concentrated blood, leucocyte concentrated blood, and platelet rich plasma can be collected. Furthermore, concentrated platelet liquid and platelet poor plasma can be obtained from the platelet rich plasma obtained above.

According to the present invention, substances toxic to organisms can also be removed from platelet rich plasma by using an absorption column in which an activated carbon, an ion exchange resin, alumina or the like is packed or an affinity column in which an antigen-antibody reaction is carried out, whereby the desired therapeutic purposes can be attained. Since the blood component separation operation according to the present invention can be readily carried out even in, for example, small room, it is extremely advantageous for plasma exchange therapy and plasma purification therapy for patients having a diffuse collagen disease such as rheumatoid arthritis showing the sthenia of erythrocyte sedimentation rate and cancer patients.

The invention has been described in detail with particular reference to certain preferred embodiments thereof, but it will be understood that variations and modifications can be effected by those skilled in the art within the spirit and scope of the invention.

The present invention will now be further illustrated by, but is by no means limited to, the following examples.

EXAMPLE 1

Blood separation apparatuses as shown in FIG. 1 and Table 1 were manufactured using acrylic resin for the vessel and the blood flow channel plates and using stainless steel for blood feed line and discharge lines.

Figure 7:
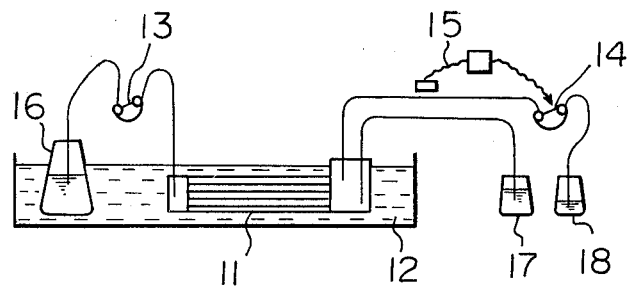
FIG. 7 is a schematic view illustrating one embodiment of the blood component separation system for an experimental practice of the present invention.

Blood component separation systems as shown in FIG. 7 are assembled by using the apparatuses manufactured above. Porcine blood containing heparin added for preventing the coagulation and having a temperature of 37° C. was fed through a blood feed line at a flow rate of 5.2 ml/min, whereby the blood components were separated. The results are shown in Table 1 below.

TABLE 1

| Exp. No. | Total Volume of Vessel (cm³) | Area of Flow Channel (cm²) | Thickness of Flow Channel (mm) | Number of Flow Channel | Residence Time in Blood Channel (min) | Volume of Second Empty Space (cm³) | Residence Time in Empty Space (B) (min) | Flow Rate of Platelet Rich Plasma Obtained (ml/min) | Separation Efficiency (%) |
|---|---|---|---|---|---|---|---|---|---|
| 1* | 75.5 | 10 × 13 | 2 | 2 | 10 | 13.5 | 2.6 | 1.6 | 31 |
| 2* | 149 | 10 × 13 | 2 | 5 | 25 | 7.3 | 1.4 | 0.8 | 15 |
| 3** | 78.5 | 10 × 13 | 1 | 5 | 12.5 | 7.3 | 1.4 | 0.8 | 15 |
| 4** | 78.5 | 10 × 11 | 1 | 5 | 10.6 | 13.5 | 2.6 | 1.3 | 25 |
| 5** | 78.5 | 10 × 11 | 1 | 5 | 10.6 | 7.3 | 1.4 | 0.7 | 13 |

*Erythrocyte Sedimentation Rate 70 mm (1 hr, 37° C.)
**Erythrocyte Sedimentation Rate 45 mm (1 hr, 37° C.)

EXAMPLE 2

Blood separation apparatuses as shown in FIG. 1 and Table 2 below were manufactured using the same materials as in Example 1. The blood separation experiments of Example 1 were repeated, except that blood flow rates were changed.

The results are shown in Table 2 below.

TABLE 2

| Exp. No. | Blood flow rate (ml/min) | Total volume of vessel (cm³) | Area of flow channel (cm²) | Thickness of flow channel (mm) | Number of flow channel | Residence time in blood flow channel (min) | Volume of empty space (B) (cm³) | Residence time in blood flow channel (min) | Flow rate of platelet rich plasma obtained (ml/min) | Separation efficiency (%) |
|---|---|---|---|---|---|---|---|---|---|---|
| 1* | 16.5 | 223 | 5 × 11 | 15 | 2 | 10 | 39 | 2.4 | 2.1 | 13 |
| 2* | 15.3 | 191.5 | 5 × 11 | 5 | 5 | 9 | 36 | 2.4 | 2.4 | 16 |
| 3* | 13.8 | 180 | 10 × 11 | 2 | 5 | 8 | 35 | 2.5 | 2.9 | 21 |
| 4** | 6.9 | 89 | 10 × 11 | 1 | 5 | 8 | 25 | 3.5 | 2.3 | 33 |
| 5** | 6.9 | 76.6 | 10 × 11 | 1 | 5 | 8 | 12.6 | 1.7 | 1.2 | 17 |
| 6** | 13.8 | 95.5 | 10 × 11 | 1 | 5 | 4 | 31.5 | 2.3 | 3.6 | 26 |

*Erythrocyte Sedimentation Rate 55 mm (1 hr, 37° C.)
**Erythrocyte Sedimentation Rate 63 mm (1 hr, 37° C.)

EXAMPLE 3

Figure 6:
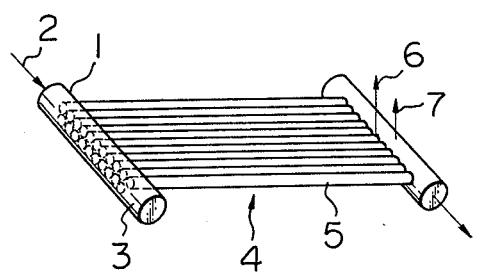
FIG. 6 is a schematic view illustrating one embodiment of the blood component separation apparatus having a plurality of the tubular type blood channels.

Blood separation apparatuses as shown in FIG. 6 and Table 3 were manufactured using acrylic resin for the vessel and using stainless steel pipes for the blood feed line, the blood discharge lines and the tubular blood flow channels.

Blood component separation systems as shown in FIG. 7 were assembled by using the apparatuses manufactured above. Porcine blood containing heparin added to prevent the coagulation and having a temperature of 37° C. were fed through the blood feed line at a flow rate of 1.5 ml/min, whereby the blood components were separated. The results are shown in Table 3 below.

TABLE 3

| Exp. No. | Total Volume of Vessel (cm³) | Diameter of Pipe (mm) | Length of Pipe (cm) | Number of Pipe | Volume of Second Empty Space (cm³) | Flow Rate of Plate Rich Plasma Obtained (ml/min) |
|---|---|---|---|---|---|---|
| 1* | 13.7 | 2 | 12 | 20 | 3.1 | 0.42 |
| 2* | 16.2 | 2 | 12 | 40 | 0.6 | 0.15 |
| 3** | 14.1 | 1 | 10 | 100 | 3.1 | 0.54 |
| 4** | 21.0 | 5 | 15 | 5 | 3.1 | 0.31 |
| 5** | 59.4 | 15 | 30 | 1 | 3.1 | 0.16 |

*Erythrocyte Sedimentation Rate 20 mm (1 hr, 37° C.)
**Erythrocyte Sedimentation Rate 45 mm (1 hr, 37° C.)

EXAMPLE 4

The blood separation experiments were carried out by using the apparatus having the structure of experiment No. 6 of Example 2. The temperature of the apparatus was maintained at 37° C. Porcine blood containing heparin added to prevent the coagulation and having a temperature of 38° C. was fed through the blood feed line at a flow rate of 10 ml/min, while a water-soluble polymer is simultaneously added to the blood. The erythrocyte sedimentation rate of the porcine blood was 43 mm at 37° C.

The following water-soluble polymers were used.

Gelatin Derivatives

GELAFSIN (manufactured by Toyo Jyozo Co. in Japan; polymerization product of decomposed gelatin 4%, sodium chloride 0.852% and calcium dichloride 0.074 g)

Polysaccharide

DEXTRAN 70 (dextran intravenous infusion manufactured by Otsuka Kojyo in Japan; dextrose 5%, dextran 70 (M. W. about 70,000) 6%)

DEXTRAN 40 (low molecular dextran intravenous infusion manufactured by Otsuka Kojyo in Japan; dextrose 5%, dextran 40 (M. W. about 40,000) 10%)

The results are shown in Table 4 below.

TABLE 4

| Exp. No. | Aqueous Water-soluble Polymer Solution Type | Flow Rate | Flow Rate of Platelet Rich Plasma (ml/min) | Separation Efficiency* (%) |
|---|---|---|---|---|
| 1 | GELAFSIN | 2 ml/min | 6.4 | 44 |
| 2 | DEXTRAN 70 | " | 5.3 | 33 |
| 3 | DEXTRAN 40 | " | 5.9 | 39 |
| 4 | — | — | 2.9 | 29 |

*Separation efficiency = 
$$\frac{\text{(Flow rate of platelet rich plasma)} - \text{(Flow rate of aqueous water-soluble polymer solution)}}{\text{(Flow rate of blood containing anticoagulant)}} \times 100$$

We claim:

1. An apparatus for separating blood components by means of sedimentation action due to gravitational force, comprising:
   a first empty space provided with an opening for a feed line of blood;
   a component separation portion connected with said empty space, the inside of the separation portion forming a plurality of flat flow channels having a thickness of not more than 20 mm.; and
   a second empty space provided with at least two openings for discharge lines of the separated blood components.

2. An apparatus as claimed in claim 1, wherein two openings for the discharge lines are located at two different heights in the empty space having the openings for the discharge of the separated blood components.

3. An apparatus as claimed in claim 1, wherein three openings for the discharge lines are located at different heights in the empty space having the openings for the discharge of the separated blood components.

4. An apparatus as claimed in claim 1, wherein a weir is mounted at an intermediate height in the empty space having the openings for the discharge of the separated blood components in such a manner that the weir blocks a portion of the blood flow and wherein one opening for the discharge line is located at an intermediate height at the upstream side of the weir and at least one opening for the discharge line is located at the downstream side of the weir.

5. An apparatus for separating blood components by means of sedimentation action due to gravitational force, comprising:
   a first empty space provided with an opening for a feed line of blood;
   a component separation portion connected with said empty space, the inside of the separation portion forming a plurality of tubular blood flow channels having a sectional area of not more than 3 cm$^2$; and
   a second empty space provided with at least two openings for discharge lines of the separated blood components.

6. An apparatus as claimed in claim 5, wherein two openings for the discharge lines are located at two different heights in the empty space having the openings for the discharge of the separated blood components.

7. An apparatus as claimed in claim 5, wherein three openings for the discharge lines are located at different heights in the empty space having the openings for the discharge of the separated blood components.

8. An apparatus as claimed in claim 5, wherein a weir is mounted at an intermediate height in the empty space having the openings for the discharge of the separated blood components in such a manner that the weir blocks a portion of the blood flow and wherein one opening for the discharge line is located at an intermediate height at the upstream side of the weir and at least one opening for the discharge line is located at the downstream side of the weir.

9. A method for separating blood components by means of sedimentation action due to gravitational force, comprising the steps of:
   continuously passing blood to be separated through a blood flow channel comprising at least two flat empty spaces having a thickness of not more than 20 mm, said blood containing an added water-soluble polymer, while the blood flow channel is filled up;
   separating the blood flow into multiple streams of the separated blood component layers; and
   collecting the desired blood component layer or layers.

10. A method as claimed in claim 9, wherein the molecular weight of said water-soluble polymer is more than 1000 but less than 100,000.

11. A method for separating blood components by means of sedimentation action due to gravitational force, comprising the steps of:
    continuously passing blood to be separated through a blood flow channel comprising at least two tubular spaces having a sectional area of not more than 3 cm$^2$, said blood containing an added water-soluble polymer, while the blood flow channel is filled up;
    separating the blood flow into multiple streams of the separated blood component layers; and
    collecting the desired blood component layer or layers.

12. A method as claimed in claim 11, wherein the molecular weight of said water-soluble polymer is more than 1000 but less than 100,000.

* * * * *